United States Patent [19]
Smith

[11] 4,092,368
[45] May 30, 1978

[54] VAPOR PHASE TRANSESTERIFICATION

[75] Inventor: William E. Smith, Schenectady, N.Y.

[73] Assignee: General Electric Company, Pittsfield, Mass.

[21] Appl. No.: 450,588

[22] Filed: Mar. 13, 1974

[51] Int. Cl.$^2$ .................... C07C 29/00; C07C 27/00
[52] U.S. Cl. .................................. 568/877; 560/234
[58] Field of Search ................... 260/638 R, 491; 560/234

[56] References Cited
U.S. PATENT DOCUMENTS

| | | | |
|---|---|---|---|
| 1,433,308 | 10/1922 | Steffens | 260/491 |
| 3,328,439 | 6/1967 | Hamilton | 260/638 R |

*Primary Examiner*—Joseph E. Evans
*Attorney, Agent, or Firm*—William F. Mufatti

[57] ABSTRACT

A vapor phase process for preparing allylic alcohols which comprises reacting an allylic ester of a lower alkyl carboxylic acid with a lower alkanol in the presence of a zeolite transesterification catalyst.

2 Claims, No Drawings

VAPOR PHASE TRANSESTERIFICATION

This invention relates to a process for preparing allylic alcohols which comprises reacting an allylic ester of a lower alkyl carboxylic acid with a lower alkanol in the vapor phase and in the presence of a zeolite transesterification catalyst.

BACKGROUND OF THE INVENTION

Allyl alcohol has been prepared by a number of different methods. Most prominent among them are the rearrangement of propylene oxide (French Pat. No. 1,496,221) and the hydrolysis of allyl chloride (Japanese Pat. No. 70-10,126) and allyl acetate (Japanese Pat. No. 73-10,767). The latter two methods particularly are suitable for preparation of a variety of allylic alcohols.

The liquid phase methanolysis of allyl acetate under the influence of metal alkoxide and hydroxide catalysts has also been described (German Pat. No. 1,939,142). With this method, however, the catalyst is gradually consumed in side reactions and is not conveniently recycled.

DESCRIPTION OF THE INVENTION

It has been discovered that allylic alcohols may be produced with high efficiency by reaction of the corresponding carboxylate esters with lower alkanols in the vapor phase and in the presence of a zeolite transesterification catalyst. In addition to the advantages inherent in a stationary, heterogenous catalyst, the zeolites of this process are selective with respect to the transesterification reaction and are not subject to destruction in side reactions.

The process is illustrated for the case of preparation of allyl alcohol by methanolysis of allyl acetate in Equation (1):

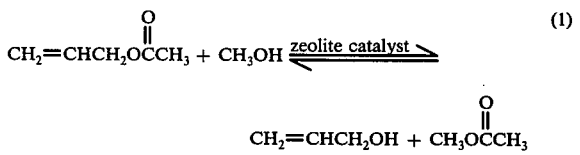

The process may be employed for the production of a wide variety of allylic alcohols. Allyl alcohol, methallyl alcohol and crotyl alcohol in particular are efficiently produced in this way, derived from the corresponding allyl, methallyl and crotyl carboxylate esters. The carboxylate moieties in these esters are those derived from the lower alkyl carboxylic acids, i.e., those having from one to six carbon atoms. A preferred class of carboxylate esters is the acetates. The lower alkanol may be selected from those having from one to six carbon atoms, with methanol a preferred alkanol.

The catalysts that may be employed in this invention are selected from the natural and snythetic zeolites that are well known in the art and are detailed in *Molecular Sieves*, Charles K. Hersh, Reinhold Publishing Company, New York (1961), which is incorporated herein by reference. Representative natural zeolites which may be employed in the instant invention include those in Table 3-1 on page 21 of the Hersh reference. Additional zeolite catalysts are set forth in *Organic Catalysis Over Crystalline Aluminosilicates*, P.B. Venuto and P.S. Landis, Advances in Catalysis, Vol. 18, pp. 259 to 371 (1968), incorporated herein by reference.

Particularly useful catalysts are those designated by the Linde Division of the Union Carbide Corporation as zeolite types A, X and Y, described in U.S. Pat. Nos. 2,882,242, 2,882,243, 3,130,007 and 3,529,033, which are incorporated herein by reference. Other zeolites are of course included within the scope of this invention.

The temperatures at which the process can be carried out vary widely. Temperatures ranging from about 150° C. to about 300° C. are generally adequate although higher temperatures can be used. Preferably, the reaction is carried out at temperatures of from about 180° C. to about 250° C. The maximum depends upon destruction of the product, elimination reactions occurring under too vigorous conditions.

Although only atmospheric pressure is normally required, it will be of course apparent to those skilled in the art that superatmospheric or subatmospheric pressure may be used where conditions so dictate.

In carrying out the process, a vapor phase mixture of the allylic ester and alkanol (the latter usually in substantial excess) is passed through a heated bed of the zeolite catalyst. The effluent is distilled directly, affording the allylic alcohol and alkyl ester products, in addition to the alkanol and unconverted allylic ester, which are recycled to the reaction zone. In the case of preparing allyl alcohol by methanolysis of allyl acetate particularly, the methyl acetate-methanol azeotrope, methanol, allyl alcohol and allyl acetate are easily separated by simple distillation, a situation much more favorable than when water is present as in hydrolysis processes.

As described in copending applications of William E. Smith and R. John Gerhart, Ser. Nos. 439,275, 439,276 and 439,277, all filed Feb. 4, 1974 and now abandoned and all assigned to the same assignee as the instant invention, carboxylic acid esters can be employed as feedstock in processes for preparing allylic esters by oxidation of the appropriate olefins. Thus, with recycle of the alkyl carboxylate co-product an efficient and economical overall process for producing allylic alcohols from olefins is possible, as illustrated in Equations (2) and (3) for the case of preparing allyl alcohol from propylene:

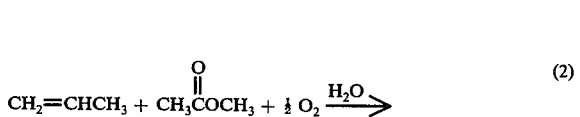

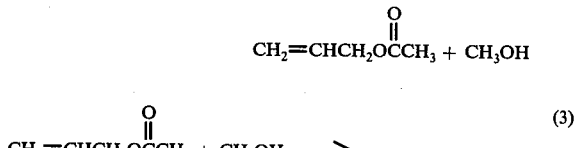

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

APPARATUS

A vertical hot tube reaction (16 mm ID × 70 cm effective length) was constructed from heavy wall glass, with 24/40 male and female joints. Vigreaux points were indented just above the male joint to support catalyst pellets. Thermocouple leads were fastened into three other Vigreaux indentations at points along the length. Three 4 ft. × 1 in. Briskheat glass insulated heating tapes were wound onto the tube, covered with glass wool and glass tape, and connected to separate variable transformers. The tube exit was connected by a gooseneck (also heated) to an efficient condenser and collection vessel. A three-necked flask served as the evaporator, with the reactants added from an addition funnel in a side neck. A nitrogen carrier gas was passed through to provide contact times on the order of 3 to 10 seconds.

EXAMPLES

The tube described above was charged with 113 g. of Linde catalyst 13 × (⅛ in. extruded pellets). After pretreatment with 150 ml. of methanol at 210°–240° C., the tube was maintained at that temperature range while a mixture of 50 g. of allyl acetate and 75 ml. of methanol was passed through over one hour. Direct quantitative glpc analysis of the effluent (chlorobenzene added as internal standard) showed the presence of 15.4 g. of allyl acetate (31% unconverted), and 18.8 g. of allyl alcohol (94% yield based on 69% conversion). An approximately corresponding amount of methyl acetate was also detected.

The data for this Example and a number of others is summarized in Table I.

TABLE I

Vapor Phase Zeolite - Promoted Methanolysis of Allyl Acetate

| Catalyst (Cation) | T, ° C | Conversion$^b$, % | Yield$^c$, % | WHSV$^d$ |
|---|---|---|---|---|
| 3A (K$^{30}$) | 210–240 | 50 | 100 | .54 |
| 4A (Na$^+$) | 210–240 | 43 | 91 | .53 |
|  | 280–300 | 48 | 81 | .53 |
| 5A (Ca$^{++}$) | 210–240 | 15 | 88 | .55 |
| 13X (Na$^+$) | 210–240 | 69 | 94 | .44 |

$^a$50 g allyl acetate, 75 ml methanol, single pass
$^b$A conversion of 70% corresponds to statistically complete equilibration.
$^c$Allyl alcohol
$^d$Weight hourly space velocity, allyl acetate It should, of course, be apparent to those skilled in the art that changes may be made in the particular embodiments of the invention described which are within the full intended scope of the invention as defined by the appended claims.

What is claimed is:

1. A vapor phase process for preparing an allylic alcohol which comprises reacting an allylic ester of a lower alkyl carboxylic acid selected from the group consisting of allyl acetate, methallyl acetate or crotyl acetate with methanol in the presence of a zeolite transesterification catalyst at a temperature of from about 150° C to about 300° C.

2. A vapor phase process for preparing allyl alcohol which comprises reacting allyl acetate with methanol in the presence of a zeolite transesterification catalyst at a temperature of from about 150° C to about 300° C.

* * * * *

UNITED STATES PATENT AND TRADEMARK OFFICE
CERTIFICATE OF CORRECTION

PATENT NO. : 4,092,368
DATED : May 30, 1978
INVENTOR(S) : William Edward Smith

It is certified that error appears in the above-identified patent and that said Letters Patent are hereby corrected as shown below:

Col. 3, line 1, "reaction" should be -- reactor --

Col. 4, Table I, first entry under "(Cation)" should be deleted and -- ($K^+$) -- inserted in its place.

Signed and Sealed this

Seventh Day of November 1978

[SEAL]

Attest:

RUTH C. MASON
Attesting Officer

DONALD W. BANNER
Commissioner of Patents and Trademarks